US006569675B2

(12) United States Patent
Wall et al.

(10) Patent No.: US 6,569,675 B2
(45) Date of Patent: May 27, 2003

(54) CELL CULTIVATING FLASK AND METHOD FOR USING THE CELL CULTIVATING FLASK

(75) Inventors: Joseph C. Wall, Southborough, MA (US); George F. Lyman, Kennebunkport, MA (US)

(73) Assignee: Corning Incorporated, Corning, NY (US)

(*) Notice: Subject to any disclaimer, the term of this patent is extended or adjusted under 35 U.S.C. 154(b) by 48 days.

(21) Appl. No.: 09/882,919

(22) Filed: Jun. 15, 2001

(65) Prior Publication Data

US 2001/0055803 A1 Dec. 27, 2001

Related U.S. Application Data

(60) Provisional application No. 60/212,163, filed on Jun. 16, 2000.

(51) Int. Cl.[7] .................................................. C12M 3/04
(52) U.S. Cl. ................. 435/304.2; 435/395; 435/304.3; 435/294.1
(58) Field of Search ............................ 435/288.1, 288.2, 435/288.3, 288.4, 288.5, 297.5, 299.2, 304.3, 305.1–305.4, 294.1, 394, 395; 472/102; 220/501; 215/380

(56) References Cited

U.S. PATENT DOCUMENTS

| 3,843,454 A | 10/1974 | Weiss ........................ 195/127 |
| 3,853,712 A | 12/1974 | House et al. ............... 195/127 |
| 3,870,602 A | * 3/1975 | Froman et al. ............. 215/380 |
| 4,172,013 A | 10/1979 | Skoda et al. ................ 435/240 |
| 4,228,243 A | * 10/1980 | Iizuka ..................... 435/294.1 |
| 4,307,193 A | 12/1981 | Iizuka ........................ 435/68 |
| 4,343,904 A | 8/1982 | Birch et al. ................ 435/240 |
| 4,377,639 A | 3/1983 | Lee ............................ 435/285 |
| 4,734,373 A | 3/1988 | Bartal ........................ 435/296 |

(List continued on next page.)

FOREIGN PATENT DOCUMENTS

| EP | 0 500 549 B1 | 4/1992 |
| EP | 0 481 820 B1 | 12/1996 |
| GB | 1 539 263 | 1/1979 |
| JP | 63233779 | 9/1988 |
| WO | WO 89/12676 | 12/1989 |
| WO | WO 99/33714 A1 | 7/1999 |
| WO | WO 00/78920 A1 | 12/2000 |

OTHER PUBLICATIONS

NUNC Brand Products–Nunc Cell Factory—Instruction (http://nunc.nalgenunc.com/resource/technical/techinfo/17.html) 2 pages downloaded Jun. 11, 2001.
NUNC Brand Products–Nunclon(TM) Delta Triple Flask Culturing Technique (http://nunc.nalgenunc.com/resource/technical/technotes/1–02.html) 3 pages downloaded Jun. 11, 2001.

*Primary Examiner*—William H. Beisner

(57) ABSTRACT

The present invention includes a cell cultivating flask and a method for growing cells within the cell cultivating flask which is configured such that a user can directly access the individual trays or cell growing areas within the cell cultivating flask. Basically, the cell cultivating flask includes a cover located on top of an intermediate tray which is located on top of a bottom tray. The intermediate tray and bottom tray each have a bottom plate and side walls that define a cell growth area. And, the cover and intermediate tray each have a neck with an opening formed therein which enables a user to directly add or remove a cell cultivating media to or from each of the cell growth areas in the intermediate tray and the bottom tray. The cell cultivating flask may have more than one intermediate tray.

24 Claims, 13 Drawing Sheets

U.S. PATENT DOCUMENTS

| | | | |
|---|---|---|---|
| 5,034,124 A | 7/1991 | Kopf | 210/231 |
| 5,112,957 A * | 5/1992 | Pollard | 204/462 |
| 5,151,366 A | 9/1992 | Serkes et al. | 435/285 |
| 5,240,854 A | 8/1993 | Berry et al. | 435/284 |
| 5,272,084 A | 12/1993 | O'Connell et al. | 435/240.243 |
| 5,310,676 A | 5/1994 | Johansson et al. | 435/285 |
| 5,843,766 A | 12/1998 | Applegate et al. | 435/284.1 |
| 5,955,344 A | 9/1999 | Copeland et al. | 435/243 |
| 6,022,742 A | 2/2000 | Kopf | 435/281 |
| 6,107,085 A | 8/2000 | Coughlin et al. | 435/299.1 |
| 6,143,508 A | 11/2000 | Okarma | 435/7.21 |
| 6,197,573 B1 | 3/2001 | Suryanarayan et al. | 435/286.7 |
| 6,204,051 B1 | 3/2001 | Copeland et al. | 435/305.4 |
| 6,214,574 B1 | 4/2001 | Kopf | 435/41 |
| 6,329,195 B1 | 12/2001 | Pfaller | 435/297.2 |
| 6,429,008 B1 | 8/2002 | Copeland et al. | 435/303.2 |

* cited by examiner

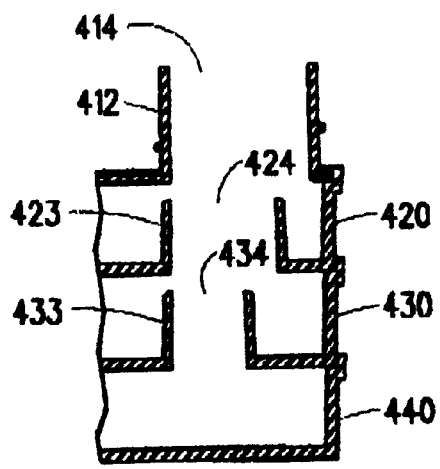
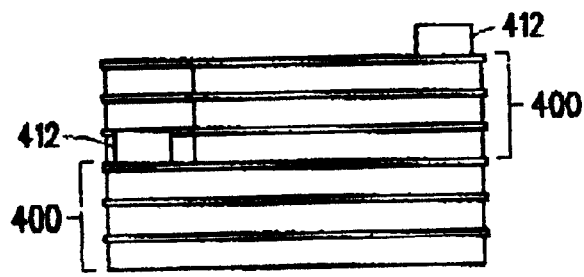
FIG. 4G          FIG. 4I
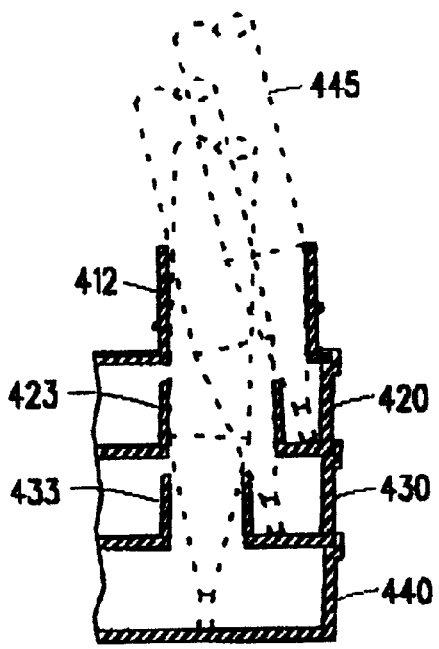
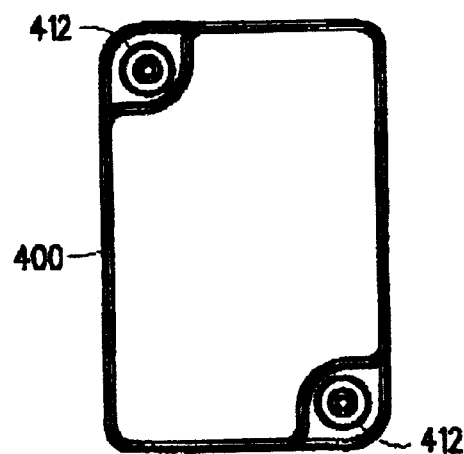
FIG. 4H          FIG. 4J

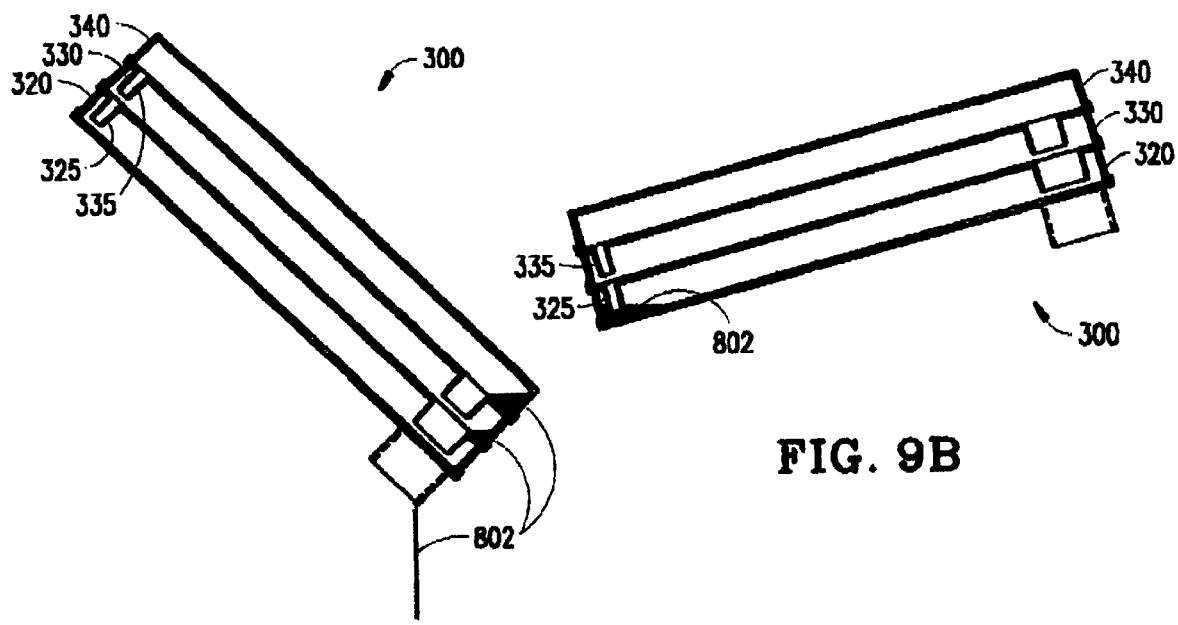
FIG. 9B
FIG. 9A
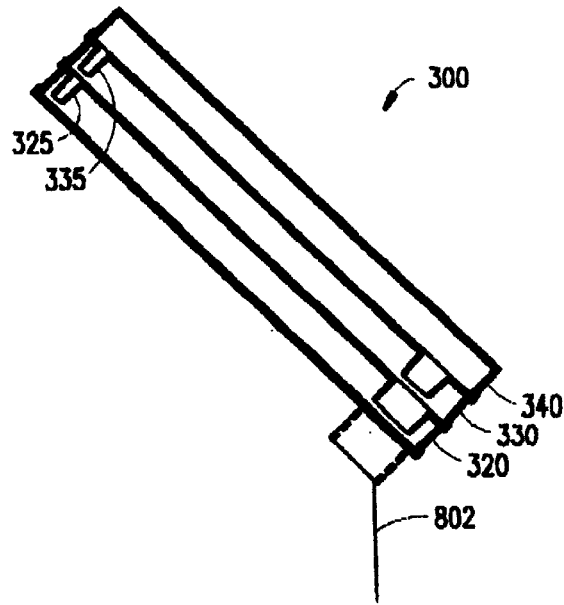
FIG. 9C

CELL CULTIVATING FLASK AND METHOD FOR USING THE CELL CULTIVATING FLASK

CLAIMING BENEFIT OF PRIOR FILED PROVISIONAL APPLICATION

This application claims the benefit of U.S. Provisional Application Ser. No. 60/212,163, filed on Jun. 16, 2000.

BACKGROUND OF THE INVENTION

1. Field of the Invention

The present invention relates in general to the cellular biological field and, in particular, to a cell cultivating flask and method for using the cell cultivating flask to grow cells.

2. Description of Related Art

Manufacturers of cell cultivating flasks have been for some time trying to design a cell cultivating flask that is more simple and convenient to use than the traditional cell cultivating devices. A cell cultivating flask is basically a device which contains one or more trays that are designed to receive a cell cultivating media and to enable the growth of cells within the cell cultivating media. Examples of two traditional cell cultivating devices are briefly discussed below and described in U.S. Pat. Nos. 5,310,676 and 4,172,013 both of which are hereby incorporated by reference herein.

Referring to FIGS. 1A and 1B (PRIOR ART), there are illustrated two perspective views of a traditional cell cultivating device described in the aforementioned U.S. Pat. No. 5,310,676. The cell cultivating device shown in FIGS. 1A and 1B comprises an outer container or flask 10, which is made from a transparent or non-transparent material, such as glass or plastics material, or from metal. The container 10 is provided with a neck 11 defining a filling opening 12. The neck 11 is formed with outer screw threads 13 for cooperating with inner screw threads of a screw cap 14 by means of which the filling opening 12 may be closed. The outer container 10 has a flat bottom wall 18, a top wall 19, opposite side walls 20, a flat end wall 21, and an opposite end wall 22 on which the neck 11 is formed.

A number of partition wall members 15 having a bottom wall or cell attachment plate 16 and a surrounding peripheral side wall 17 extending upwardly therefrom, is arranged in superposed relationship within the container 10, so as to define cultivating chambers therein. The lower partition wall member 15 arranged adjacent to the bottom wall 18 is supported by feet or spacer members 23 so that a cultivating chamber is defined between the inner surface of the container bottom wall 18 and the lower surface of the bottom wall 16 of the lower partition wall member 15. The spacer members 23 may be formed as integral parts of the walls of the outer container 10 or of the lower partition wall member. An upper cultivating chamber is defined between the inner surface of the container top wall 19 and the upper surface of the adjacent bottom wall 16 of the upper partition wall member 15. Furthermore, a cultivating chamber is defined between each pair of adjacent partition wall members 15. Thus, the cell cultivating device shown in FIGS. 1A and 1B which comprises two partition wall members 15 defines three cultivating chambers therein.

The container end wall 22 has a convex contour so that a manifold chamber 24 is defined between the container end wall 22 and the adjacent side walls 17 of the partition wall members 15. Cut-outs in the peripheral side walls 17 of the partition wall members 15 define overflow openings 26 communicating with the manifold chamber 24.

The outer container 10 may be made from at least two separate container parts, which may, for example, be molded from transparent plastics material. When the partition wall members 15 have been arranged within one of the container parts, such container parts may be sealingly interconnected, for example by interconnecting flanged rim portions of the container parts so as to form a heat seal 27 in a plane being substantially parallel with the bottom walls 16 of the partition wall members 15.

As indicated in broken lines in FIGS. 1A and 1B each of the partition wall members 15 further comprises an equalizing opening 30 formed in its peripheral side wall 17 adjacent to the container end wall 21. The equalizing opening 30 may be a cut-out formed in the rim portion of a curved part of the peripheral wall 17 of each partition wall member. The curved parts of the superposed partition wall members 15 define a transverse tunnel or passage 31 interconnecting the superposed cell cultivating chambers. The tunnel or passage 31 may have any suitable cross-sectional shape, which may, for example, be a semi-circle as shown.

When the cell cultivating device shown in FIGS. 1A and 1B is to be used it is positioned in its upright position shown in FIG. 1A, and the screw closure cap 14 is removed. A suitable amount of cell cultivating medium and cells to be cultivated are poured into the manifold chamber 24 of the container 10 through the filling opening 12 defined by the neck 11. From the manifold chamber 24 of the liquid cell cultivating medium flows into the various cultivating chambers via the overflow opening 26 and through the opening defined between the inner surface of the container bottom wall 18 and the bottom wall 16 of the adjacent partition wall member 15. Now, the level of the cell cultivating media within the cultivating chambers will be the same after a short period of time because the cultivating chambers are all interconnected by the tunnel 31 and the openings 30 formed therein. Provided that the dimensions of the cultivating chambers are substantially the same, these chambers will now contain substantially the same amount of cell cultivating media.

After the filling opening 12 has been closed by the screw cap 14, the flask 10 may then by a quick movement be tilted from the upright position shown in FIG. 1A to the position shown in FIG. 1B in which the container bottom wall 18 is supported in a substantially horizontal position. As the equalizing openings 30 are relatively small, this simple procedure renders it possible to have substantially the same amount of cell cultivating medium placed in all of the now horizontally extending cultivating chambers. This means that a layer of cell cultivating medium containing cells to be cultivated is supported by the container bottom wall 18 and by the bottom walls or cell attachment plates 16 of each of the partition wall members 15. The surfaces of these walls have preferably been subject to a surface treatment allowing good cell attachment.

After expiration of the cultivating period the cell cultivating medium may be poured out through the inlet opening 12 of the neck 11. Thereafter, the cells attached to the bottom walls 16 and 18 may be scraped or flushed out through the inlet or filling opening 12. Alternatively, the container bottom wall 18 or top wall 19, or any of the container side or end walls 20 and 21, respectively, may be cut away or otherwise removed so that the tray members may be taken out from the container 10, whereafter the cultivated cells may be scraped or flushed from the bottom walls 16 and 18.

A main drawback of this traditional cell cultivating device is that a user does not have direct access to each of the cultivating trays. In other words, the user can not fit a pipette of any size onto any cultivating tray to add or remove the cell cultivating media. Of course, it would be desirable to enable the user to have direct access to each of the cultivating trays. Another drawback of this traditional cell cultivating device is that the cell cultivating media often wicks via capillary action between the inner walls of the outer container 10 and the outer walls of the wall members 15. Cells that are trapped in this manner can easily die and contaminate the other cells.

Referring to FIGS. 2A and 2B (PRIOR ART), there are illustrated two sectional front views of a traditional cell culture system described in the aforementioned U.S. Pat. No. 4,172,013. The traditional cell culture system can be used to enable the mass growth of cell by introducing a nutrient medium, cell suspension material etc. through a central feed line 1 serving as supply channel into the lower part of a system of communicating chambers 2. As shown in FIG. 2A, the system is in a vertical position while the nutrient medium is introduced into the communicating chambers 2 which are formed by a number of parallel flat troughs 3. The nutrient medium effectively distributes itself within the communicating chambers 2 with the aid of communicating tubes (not shown) and an central aeration and evacuation channel 4 that can be used to equalize the air pressure within the communicating chambers 2. Thereafter, the nutrient medium, etc., is effectively distributed over the useful surface of the troughs 3 by moving the system into a horizontal position (see FIG. 2B) and by operating valves 5 and 6. In the horizontal position, the cells can be grown on the troughs 3 by controlling the atmosphere within the communicating chambers 2. After completion of the cell growth, the system can be restored to the vertical position which enables the grown cells and nutrient media to flow out through the central supply channel 1.

Like the traditional cell cultivating flask of FIGS. 1A and 1B, the main drawback of this traditional cell culture system is that a user does not have direct access to each of the cultivating troughs 3. In other words, the user can not fit a pipette of any size onto any cultivating trough 3 to add or remove the nutrient medium. Again, it would be desirable to enable the user to have direct access to each of the cultivating troughs 3. Another drawback of this traditional cell culture system is that the troughs 3 are so large that the system must be placed on a "very" flat surface in an incubator or the nutrient media might not sufficiently cover the trough 3 or the nutrient media may be unequal in depth. Moreover, the process of filing the system with the nutrient media, etc., and the process of changing the position of the system from vertical to horizontal and back to vertical are complicated steps that are difficult to perform and if they are not performed correctly the whole cell batch could be contaminated. Accordingly, there is a need for a cell cultivating flask that addresses the aforementioned drawbacks of the traditional cell cultivating devices. In particular, there is a need for a cell cultivating flask that enables a user to have direct access to each cultivating tray therein so as to enable the user to add or remove a cell cultivating media to or from each cultivating tray. These needs and other needs are satisfied by the cell cultivating flask and method of the present invention.

BRIEF DESCRIPTION OF THE INVENTION

The present invention includes a cell cultivating flask and a method for growing cells within the cell cultivating flask which is configured such that a user can directly access the individual trays or cell growing areas within the cell cultivating flask. Basically, the cell cultivating flask includes a cover located on top of an intermediate tray which is located on top of a bottom tray. The intermediate tray and bottom tray each have a bottom plate and side walls that define a cell growth area. And, the cover and intermediate tray each have a neck with an opening formed therein which enables a user to directly add or remove a cell cultivating media to or from each of the cell growth areas in the intermediate tray and the bottom tray. The cell cultivating flask may have more than one intermediate tray.

BRIEF DESCRIPTION OF THE DRAWINGS

A more complete understanding of the present invention may be had by reference to the following detailed description when taken in conjunction with the accompanying drawings wherein:

FIG. 4G illustrates a cut-away cross sectional view of the necks of the cell cultivating flask shown in FIG. 4A;

FIG. 4H illustrates a cut-away cross sectional view of the necks including a pipette positioned therein of the cell cultivating flask shown in FIG. 4A;

FIGS. 4I and 4J respectively illustrates a side view and a top view of two stacked cell cultivating flasks shown in FIG. 4A;

FIGS. 9A–9C illustrates cross sectional side views of the cell cultivating flask shown in FIG. 3A being emptied in accordance with a recovering operation of step 706b of the preferred method of FIG. 7.

DETAILED DESCRIPTION OF THE DRAWINGS

Figure 1A:
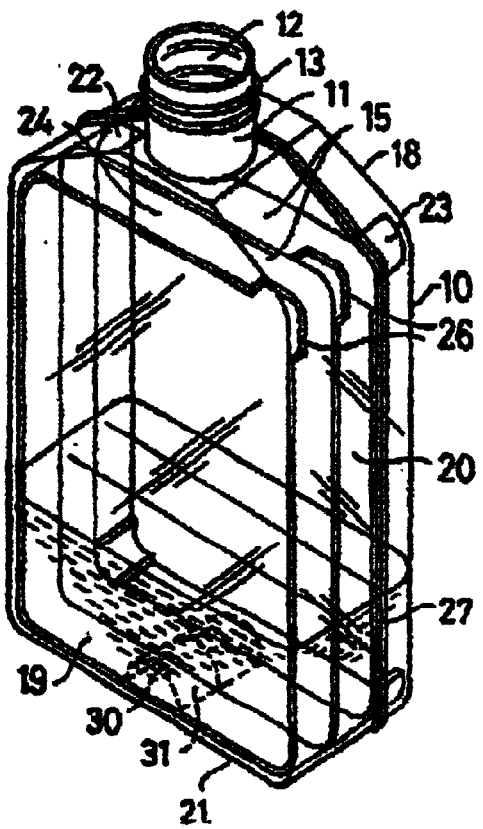
FIGS. 1A and 1B (PRIOR ART) illustrate two perspective views of a traditional cell cultivating device described in U.S. Pat. No. 5,310,676.
Figure 1B:
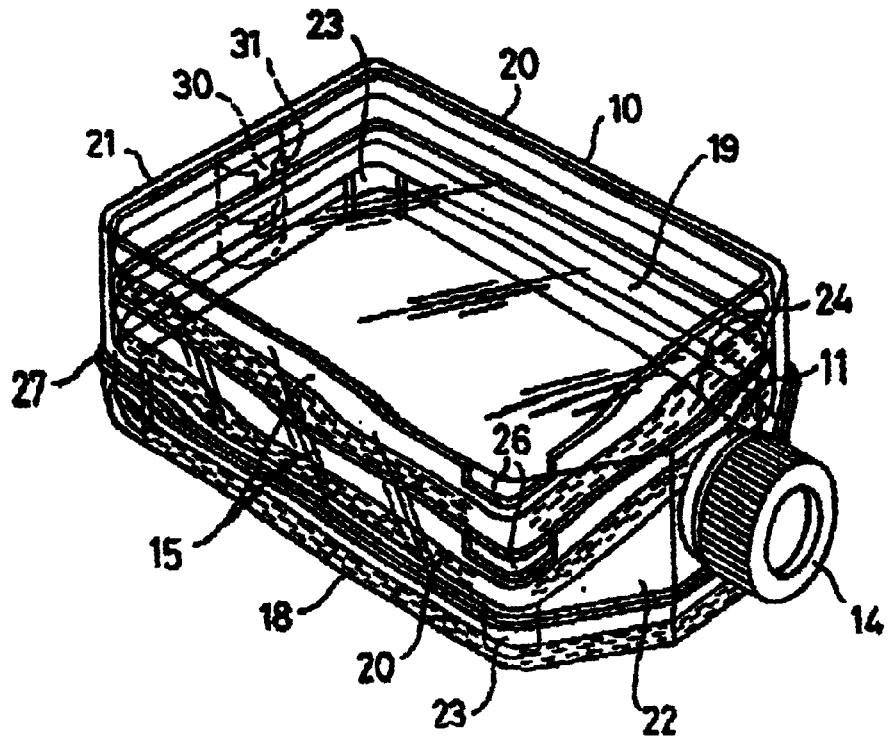
Figure 2A:
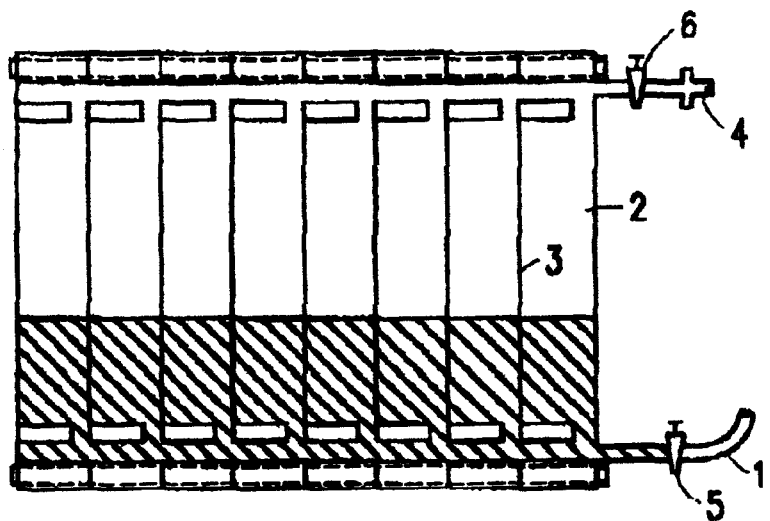
FIGS. 2A and 2B (PRIOR ART) illustrate two sectional front views of a traditional cell culture system described in U.S. Pat. No. 4,172,013.
Figure 2B:
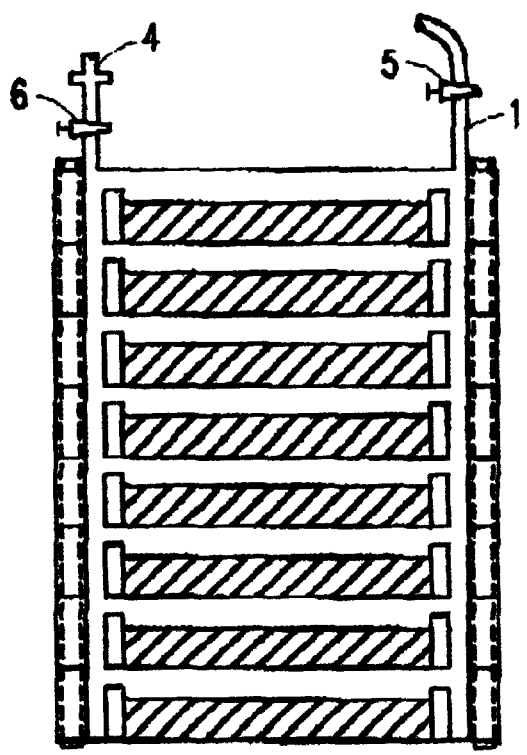

Referring to FIGS. 3A–9C, there are disclosed four embodiments of a cell cultivating flask 300, 400, 500 and 600 and a preferred method 700 in accordance with the present invention. Basically, the cell cultivating flask 300, 400, 500 and 600 is designed such that a user can have direct access to each of the trays located within the flask. More specifically, the cell cultivating flask 300, 400, 500 and 600 is designed such that the user can add or remove a cell cultivating media directly to or from each of the trays located within the cell cultivating flask. This is a marked improvement over the traditional cell cultivating devices which did not allow a user to directly access the individual trays.

Although the cell cultivating flask 300, 400, 500 and 600 is described below as having three trays on which cells can be grown, it should be understood that the cell cultivating flask of the present invention could have one tray or any number of trays on which to grow cells. Accordingly, the cell cultivating flask 300, 400, 500 and 600 and preferred method 700 should not be construed in such a limited manner.

Referring to FIGS. 3A through 3H, there are illustrated a variety of views of a first embodiment of the cell cultivating flask 300. The cell cultivating flask 300 can be made from a transparent material or a non-transparent material, such as glass or plastic materials, or from a metal. In this example, the cell cultivating flask 300 is made from a non-transparent material and includes a cover 310, two intermediate trays 320 and 330 and a bottom tray 340. The two intermediate trays 320 and 330 are stacked on top of one another and positioned between the cover 310 and the bottom tray 340 (see FIGS. 3A and 3B).

Figure 3A:
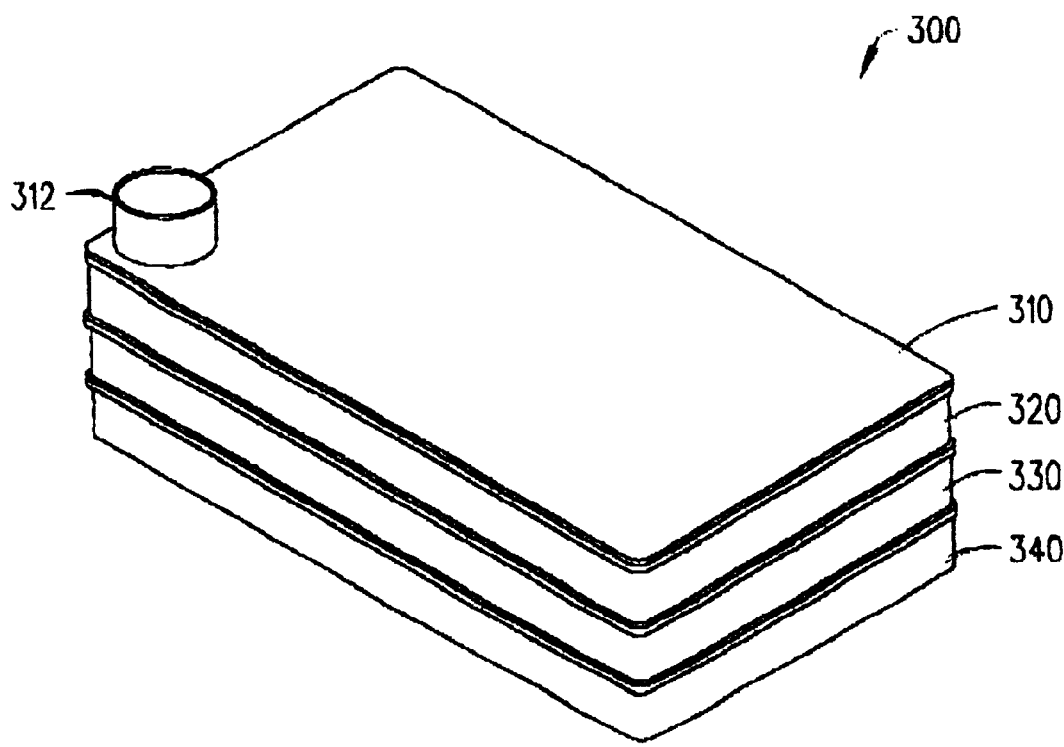
FIG. 3A illustrates a perspective view of a first embodiment of a cell cultivating flask in accordance with the present invention.
Figure 3B:
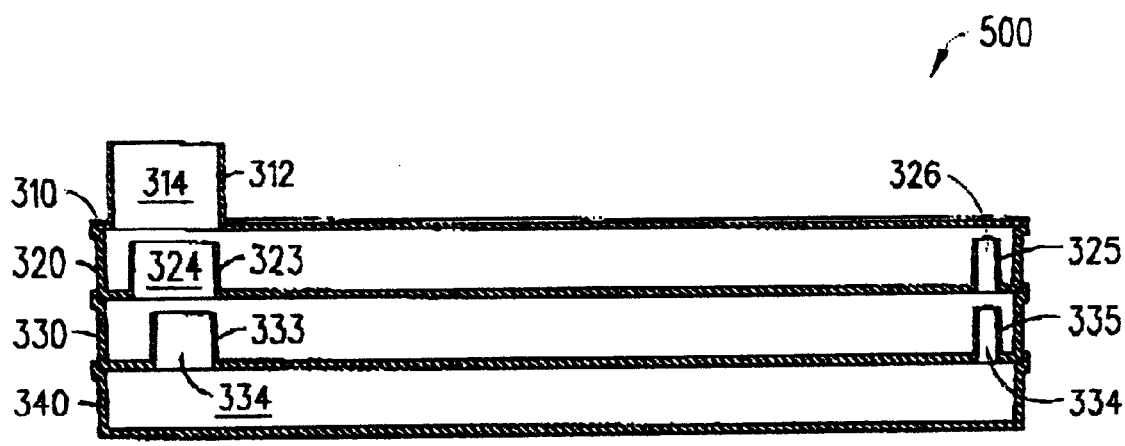
FIG. 3B illustrates a cross-sectional side view of the cell cultivating flask shown in FIG. 3A.
Figure 3C:
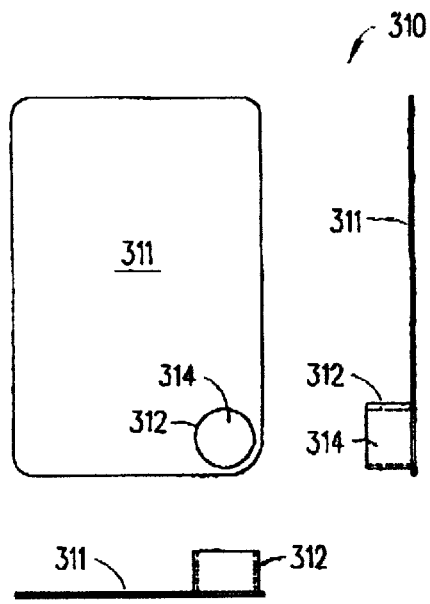
FIGS. 3C–3F respectively illustrate a top view, a cross sectional side view and a cross sectional front view of a cover, two intermediate trays and a bottom tray of the cell cultivating flask shown in FIG. 3A.
Figure 3E:
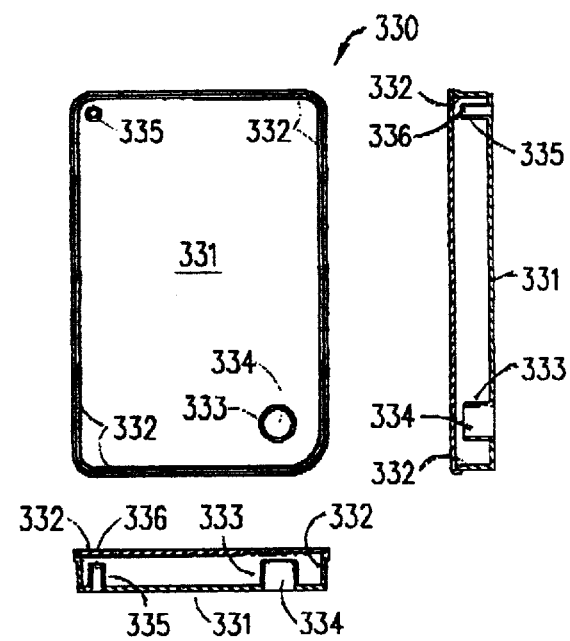
Figure 3D:
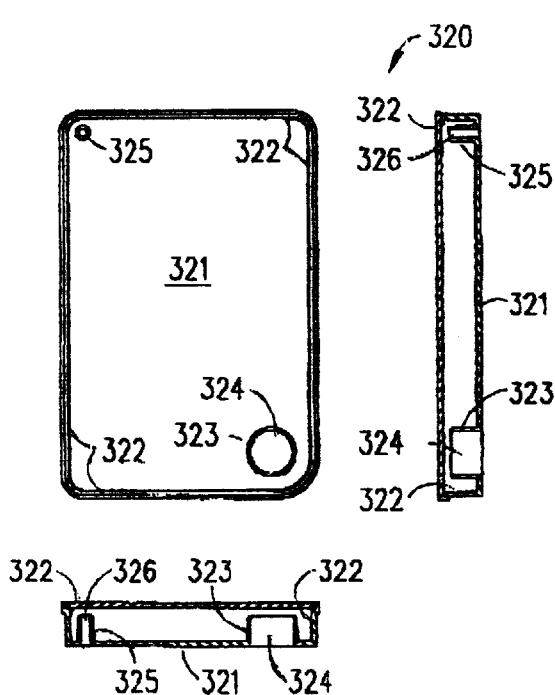

The cover 310 includes a top plate 311 having a neck 312 that defines an opening 314 that is located near a corner of the top plate 311 but it could be located anywhere on the top plate 311 (see FIG. 3C). The neck 312 could also have outer screw threads (not shown) for cooperating with inner screw threads of a neck cap (not shown)(see FIG. 4A).

The cover 310 is attached (e.g., glued, welded, snap-fitted) to the intermediate tray 320 which has a bottom plate 321 and side walls 322 that define a cell growth area. The intermediate tray 320 also includes a neck 323 that defines an opening 324 which is located below the opening 314 in the cover 310 (see FIGS. 3B and 3D). The diameter of the neck 323 in the intermediate tray 320 is smaller than the diameter of the neck 313 in the cover 310 (see FIG. 3G). The smaller neck 323 on the intermediate tray 320 enables a user to use a pipette 345 (e.g., needle, syringe, capillary or similar device) to add or remove a cell cultivating media to or from the cell growth area on the intermediate tray 320 (see FIG. 3H). The cell cultivating media includes a nutrient and cells that are to be grown on the cell growth area of the intermediate tray 320.

The intermediate tray 320 also includes an exchange tube 325 that defines an opening 326 which is shown located in an opposite corner of the neck 323. The function of the exchange tube 325 which extends up from the bottom plate 321 is described below with respect to FIGS. 8 and 9.

The intermediate tray 320 is attached (e.g., glued, welded, snap-fitted) to intermediate tray 330 which includes a bottom plate 331 and side walls 332 that define a cell growth area. The intermediate tray 330 also includes a neck 333 that defines an opening 334 which is located below the opening 324 in intermediate tray 320 (see FIGS. 3B and 3E). The diameter of the neck 333 in intermediate tray 330 is smaller than the diameter of the neck 323 in intermediate tray 320 (see FIG. 3G). The smaller neck 333 on the intermediate tray 330 enables a user to use the pipette 345 (or a similar device) to add or remove the cell cultivating media to or from the cell growth area on the intermediate tray 330 (see FIG. 3H).

Like the intermediate tray 320, the intermediate tray 330 includes an exchange tube 335 that defines an opening 336 which is shown located in an opposite corner of the neck 333. The function of the exchange tube 335 which extends up from the bottom plate 331 is described below with respect to FIGS. 8 and 9.

Figure 3F:
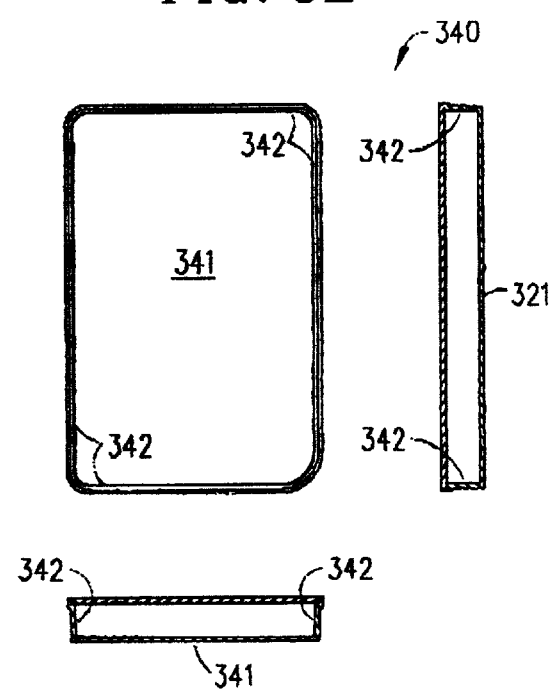
Figure 3G:
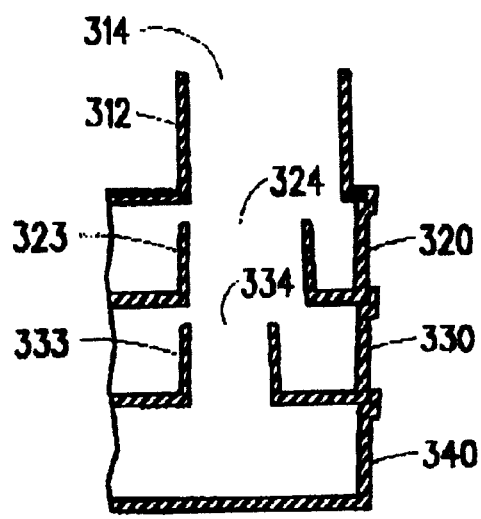
FIG. 3G illustrates a cut-away cross sectional view of the necks of the cell cultivating flask shown in FIG. 3A.

The intermediate tray 330 is attached (e.g., glued, welded, snap-fitted) to the bottom tray 340 which includes a bottom plate 341 and side walls 342 that define a cell growth area (see FIG. 3F). Like with the intermediate trays 320 and 330, the user can use the pipette 345 (or a similar device) to add or remove the cell cultivating media to or from the cell growth area on the bottom tray 340 (see FIG. 3H).

Figure 3H:
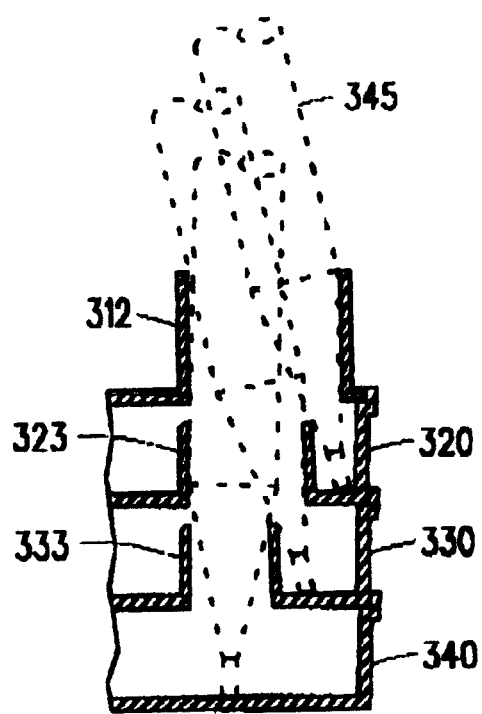
FIG. 3H illustrates a cut-away cross sectional view of the necks including a pipette positioned therein of the cell cultivating flask shown in FIG. 3A.

Referring to FIG. 3H it is shown how the user can use the pipette 345 to add or remove a cell cultivating media directly to or from each of the intermediate trays 320 and 330 and the bottom tray 340. As shown, the necks 312, 323 and 333 get progressively smaller in diameter as they move down from the cover 310 through the intermediate trays 320 and 330 towards the bottom tray 340 which enables the user to directly access each of the growth areas on the intermediate trays 320 and 330 and the bottom tray 340. The differences in the diameters of the necks 312, 323 and 333 effectively makes room for the tip of the pipette 345 to fit through one or more openings 314, 324 and 334 and make contact with any one of the cell growth areas on the intermediate trays 320 and 330 and the bottom tray 340. To further help the user to individually access each of the growth areas on the intermediate trays 320 and 330 and the bottom tray 340, the locations of the necks 312, 323 and 333 can be offset from one another on a diagonal that enables the maximum access for the pipette 345.

Referring to FIGS. 4A through 4J, there are illustrated a variety of views of a second embodiment of the cell cultivating flask 400. The cell cultivating flask 400 can be made from a transparent material or a non-transparent material, such as glass or plastic materials, or from a metal. In this example, the cell cultivating flask 400 is made from a non-transparent material and includes a cover 410, two intermediate trays 420 and 430 and a bottom tray 440. The two intermediate trays 420 and 430 are stacked on top of one another and positioned between the cover 410 and the bottom tray 440 (see FIGS. 4A and 4B).

Figure 4A:
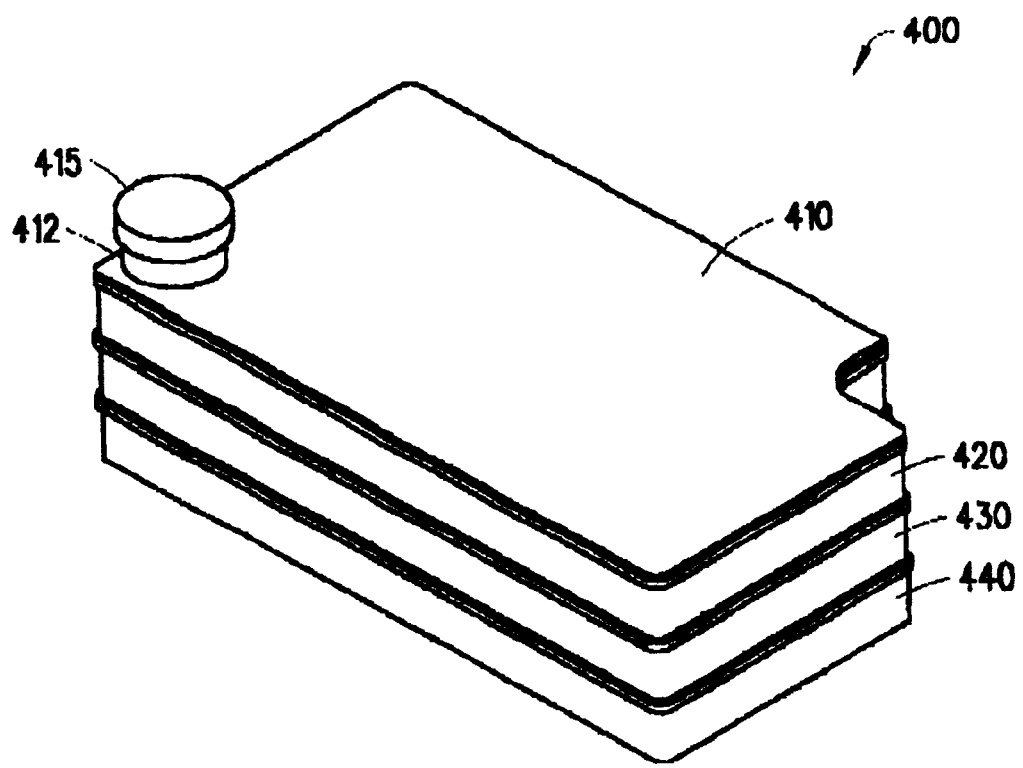
FIG. 4A illustrates a perspective view of a second embodiment of a cell cultivating flask in accordance with the present invention.
Figure 4B:
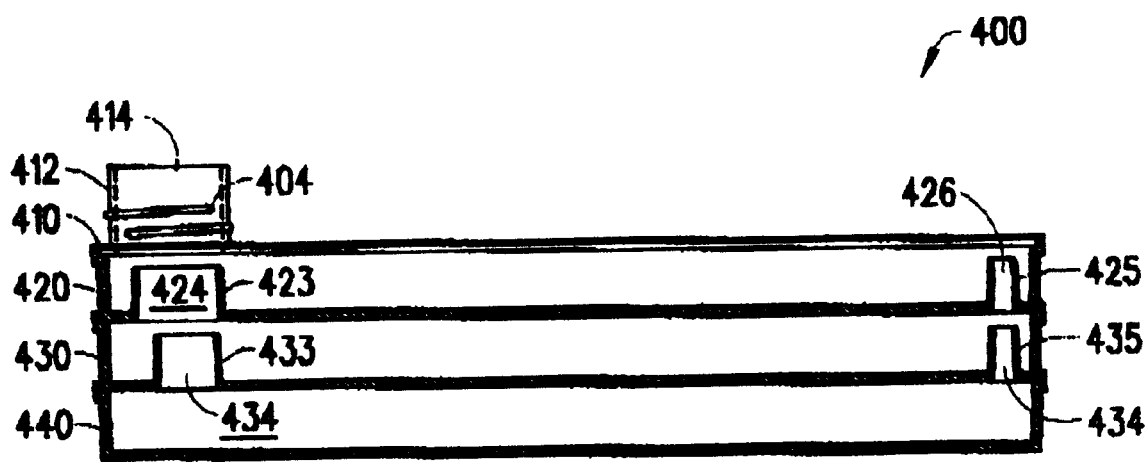
FIG. 4B illustrates a cross-sectional side view of the cell cultivating flask shown in FIG. 4A.
Figure 4C:
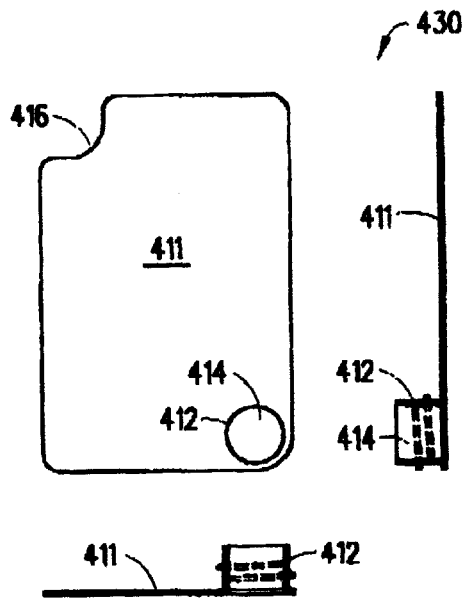
FIGS. 4C–4F respectively illustrate a top view, a cross sectional side view and a cross sectional front view of a cover, two intermediate trays and a bottom tray of the cell cultivating flask shown in FIG. 4A.
Figure 4E:
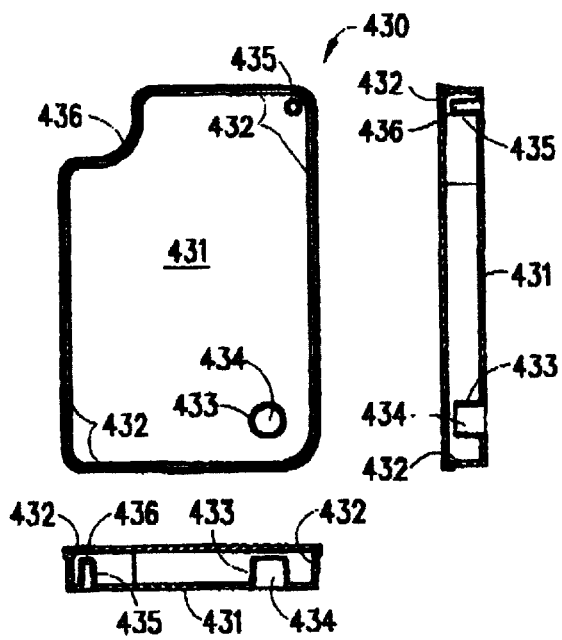
Figure 4D:
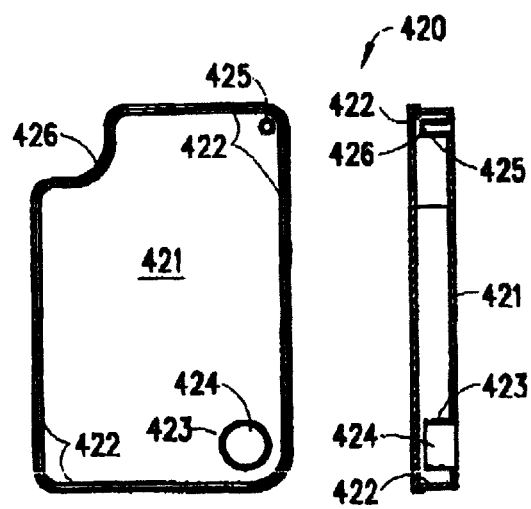
Figure 4D:
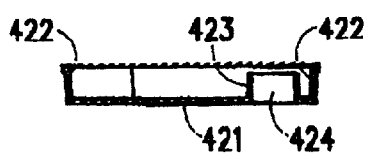

The cover 410 includes a top plate 411 having a neck 412 that defines an opening 414 that is located near a corner of the top plate 411 but it could be located anywhere on the top plate 411 (see FIG. 4C). The neck 412 could also have outer screw threads 404 for cooperating with inner screw threads of a neck cap 415 (see FIG. 4A). The neck cap 415 is configured to allow gas that was generated by growing cells to escape from the cell cultivating flask 400. The cover 410 also includes a notched corner 416 that is located in a corner opposite the neck 412.

The cover 410 is attached (e.g., glued, welded, snap-fitted) to the intermediate tray 420 which includes a bottom plate 421 and side walls 422 that define a cell growth area. The intermediate tray 420 also includes a neck 423 that defines an opening 424 which is located below the opening 414 in the cover 410 (see FIGS. 4B and 4D). The diameter of the neck 423 in the intermediate tray 420 is smaller than the diameter of the neck 412 in the cover 410 (see FIG. 4G). The smaller neck 423 on the intermediate tray 420 enables a user to use a pipette 445 (e.g., needle, syringe, capillary or similar device) to add or remove a cell cultivating media to or from the cell growth area on the intermediate tray 420 (see FIG. 4H). The cell cultivating media includes a nutrient and cells that are to be grown on the cell growth area of the intermediate tray 420.

Like the cover 410, the intermediate tray 420 includes a notched corner 426 that is located in a corner opposite the neck 423. Moreover, the intermediate tray 420 includes an exchange tube 425 that defines an opening 426 which is shown located in the other corner opposite the neck 423. The function of the exchange tube 425 which extends up from the bottom plate 421 is described below with respect to FIGS. 8 and 9.

The intermediate tray 420 is attached (e.g., glued, welded, snap-fitted) to intermediate tray 430 which includes a bottom plate 431 and side walls 432 that define a cell growth area. The intermediate tray 430 also includes a neck 433 that defines an opening 434 which is located below the opening 424 in intermediate tray 420 (see FIGS. 4B and 4E). The diameter of the neck 433 in intermediate tray 430 is smaller than the diameter of the neck 423 in intermediate tray 420 (see FIG. 4G). The smaller neck 433 on the intermediate tray 430 enables a user to use the pipette 445 (or a similar device) to add or remove the cell cultivating media to or from the cell growth area on the intermediate tray 430 (see FIG. 4H).

Like the cover 410 and intermediate tray 420, the intermediate tray 430 includes a notched corner 436 that is located in a corner opposite the neck 433. Moreover, the intermediate tray 430 includes an exchange tube 435 that defines an opening 436 which is shown located in the other corner opposite the neck 433. The function of the exchange tube 435 which extends up from the bottom plate 431 is described below with respect to FIGS. 8 and 9.

Figure 4F:
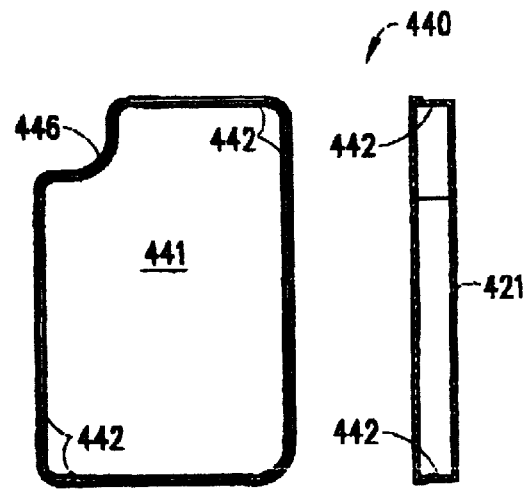
Figure 4F:

The intermediate tray 430 is attached (e.g., glued, welded, snap-fitted) to the bottom tray 440 which includes a bottom plate 441 and side walls 442 that define a cell growth area (see FIG. 4F). The bottom tray 440 also includes a notched corner 446 that is located in the same corner as the notched corners 416, 426 and 436 on the cover 410 and the intermediate trays 420 and 430. A main function of the notched corners 416, 426, 436 and 446 is described below with respect to FIGS. 4I and 4J. Like with the intermediate trays 420 and 430, the user can use the pipette 445 (or a similar device) to add or remove the cell cultivating media to or from the cell growth area on the bottom tray 440 (see FIG. 4H).

Referring to FIG. 4H it is shown how the user can use the pipette 445 to add or remove a cell cultivating media directly to or from each of the intermediate trays 420 and 430 and the bottom tray 440. As shown, the necks 412, 423 and 433 get progressively smaller in diameter as they move down from the cover 410 through the intermediate trays 420 and 430 towards the bottom tray 440 which enables the user to directly access each of the growth areas on the intermediate trays 420 and 430 and the bottom tray 440. The differences in the diameters of the necks 412, 423 and 433 effectively makes room for the tip of the pipette 445 to fit through one or more openings 414, 424 and 434 and make contact with any one of the cell growth areas on the intermediate trays 420 and 430 and the bottom tray 440. To further help the user to directly access each of the growth areas on the intermediate trays 420 and 430 and the bottom tray 440, the locations of the necks 412, 423 and 433 can be offset from one another on a diagonal that enables the maximum access for the pipette 445.

Referring to FIGS. 4I and 4J, there are respectively illustrated a side view and a top view of two stacked cell cultivating flasks 400. As illustrated, the notched corners 416, 426, 436 and 446 enables the user to stack one or more cell cultivating flasks 400 onto one another simply by rotating 180 degrees every other cell cultivating flask 400. In this way, the user can densely pack two or more cell cultivating flasks 400 and place the stack of cell cultivating flasks 400 into an incubator with practically no wasted space. Moreover, the open air space above the neck caps 415 enables an unrestricted gas exchange from the cell cultivating flasks 400. It should be understood that the cell cultivating flasks 300 of the first embodiment can also be stacked onto one another simply by rotating 90 degrees every other cell cultivating flask 300.

Figure 5A:
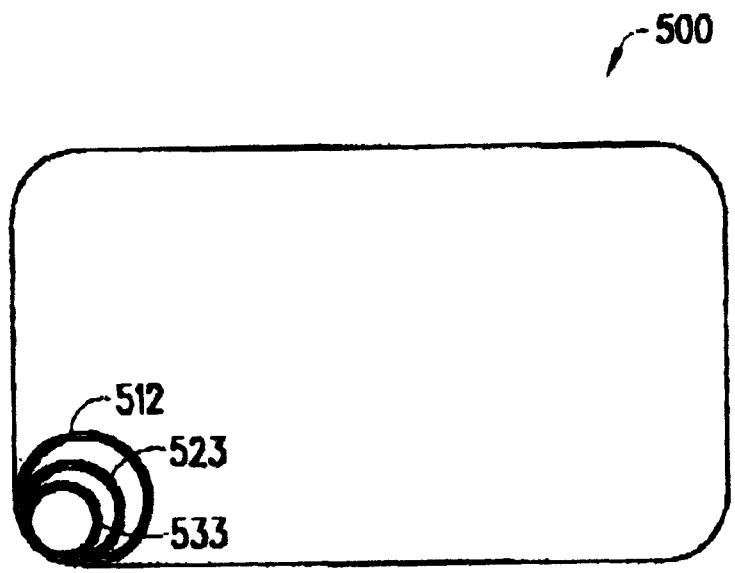
FIG. 5A illustrates a top view of a third embodiment of a cell cultivating flask in accordance with the present invention.
Figure 5B:
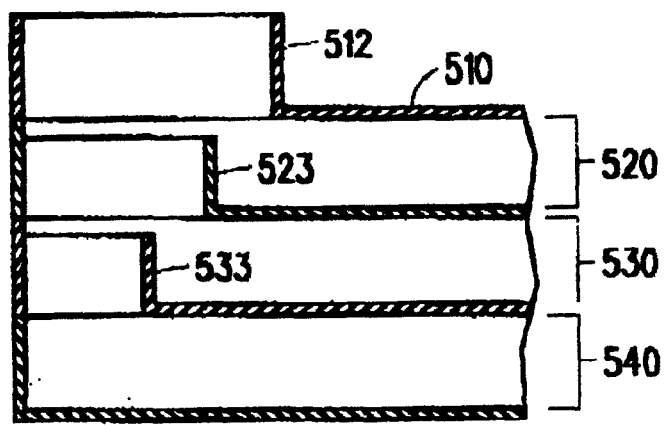
FIG. 5B illustrates a partial cross sectional side view of the necks of the cell cultivating flask shown in FIG. 5A.

Referring to FIGS. 5A–5B, there are respectively illustrated a top view and a partial cross sectional side view of a third embodiment of the cell cultivating flask 500. The cell cultivating flask 500 is similar to the first and second embodiments of the cell cultivating flasks 300 and 400 except for the location of the necks 512, 523 and 533. As illustrated, the necks 512, 523 and 533 are not located near a corner of the cell cultivating flask 500 but are instead an integral part of the corner of the cell cultivating flask 500 (compare to FIGS. 3A and 4A). It should be noted the cell cultivating flask 500 is shown without notched corners but could have notched corners similar to the notched corners 416, 426, 436 and 446 in the cell cultivating flask 400.

Figure 6A:
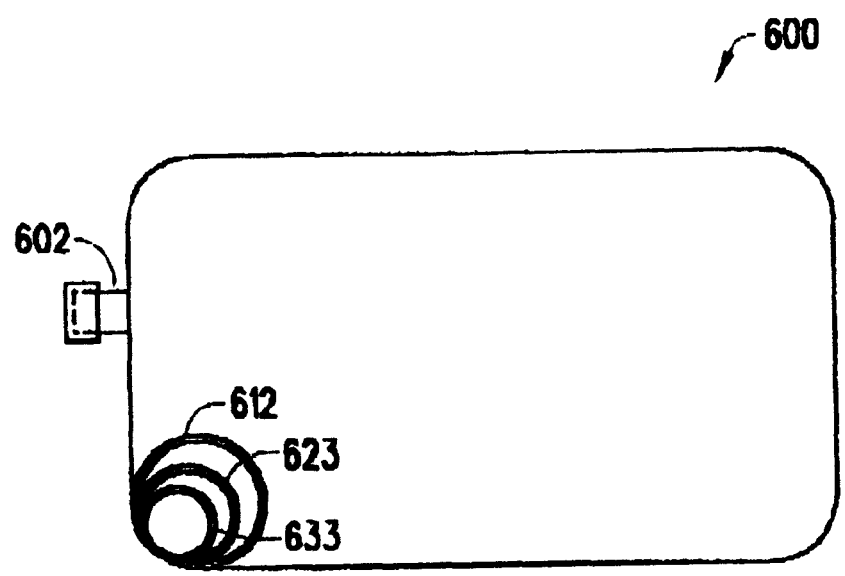
FIG. 6A illustrates a top view of a fourth embodiment of a cell cultivating flask in accordance with the present invention.
Figure 6B:
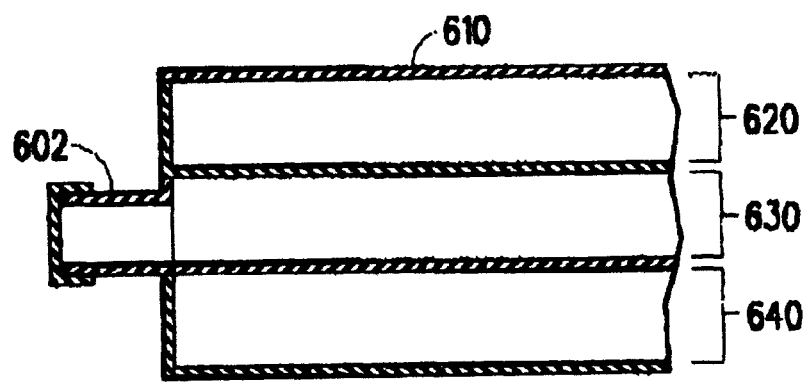
FIG. 6B illustrates a partial cross sectional side view of the additional neck in the cell cultivating flask shown in FIG. 6A.

Referring to FIGS. 6A–6B, there are respectively illustrated a top view and a partial cross sectional side view of a fourth embodiment of the cell cultivating flask 600. The cell cultivating flask 600 is similar to the first three embodiments of the cell cultivating flasks 300, 400 and 500 except for the addition of another neck 602. As illustrated, the additional neck 602 is located on the intermediary tray 630 but could also be located on the intermediary tray 620 or the bottom tray 640. A main function of the additional neck 602 is described below with respect to FIGS. 8 and 9.

It should be noted the cell cultivating flask 600 is shown without notched corners but could have notched corners similar to the notched corners 416, 426, 436 and 446 in the cell cultivating flask 400. In addition, the cell cultivating flask 600 is shown where the necks 612, 623 and 633 are an integral part of the corner of the cell cultivating flask 600, but the necks 612, 623 and 633 could be positioned as the necks in the cell cultivating flasks 300 and 400 (compare to FIGS. 3A and 4A).

Figure 7:
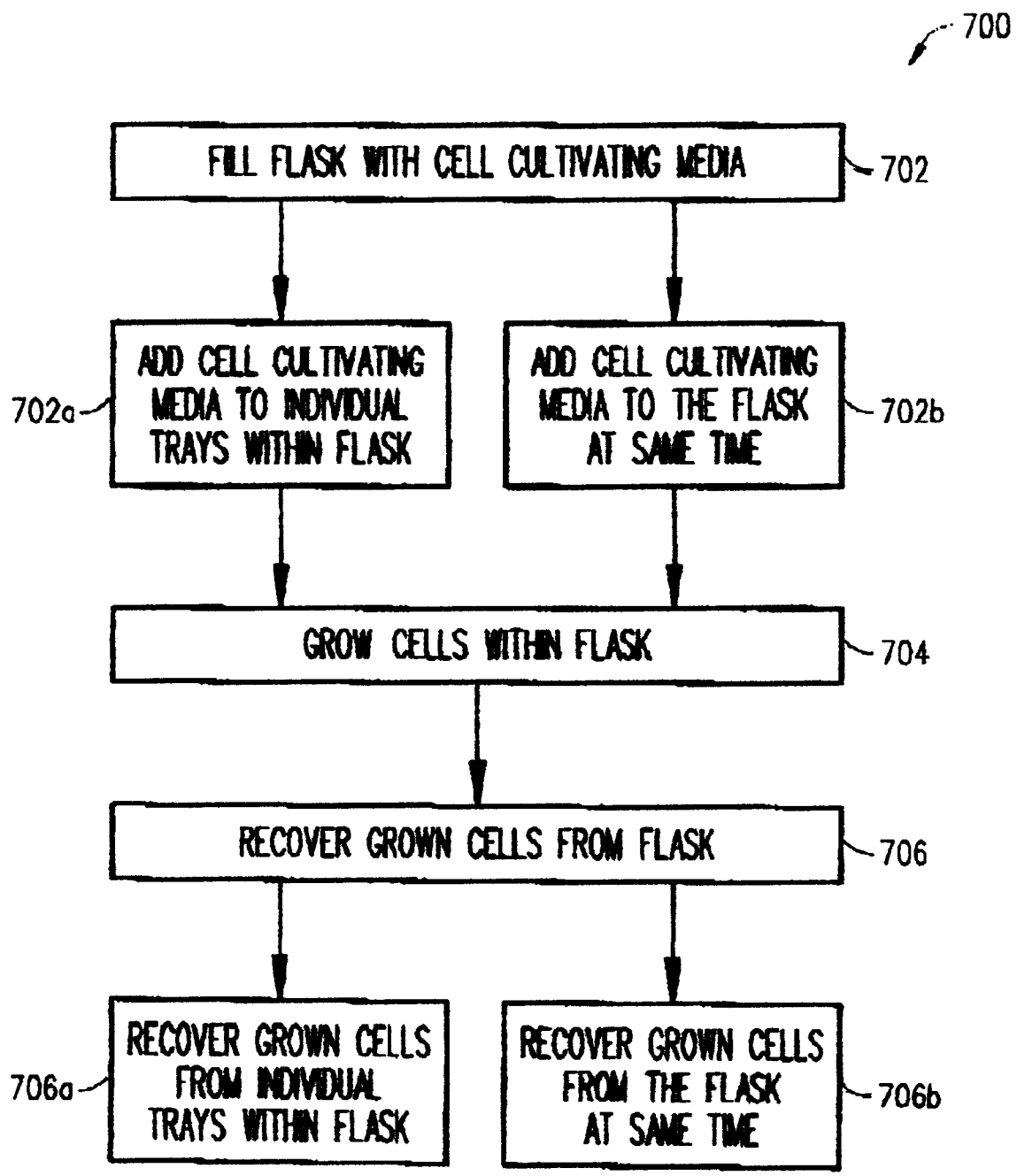
FIG. 7 is a flowchart illustrating the steps of a preferred method for using the cell cultivating flask to grow cells in accordance with the present invention.

FIG. 7 is a flowchart illustrating the steps of a preferred method for growing cells within the cell cultivating flasks 300, 400, 500 and 600 in accordance with the present invention. The different components of the cell cultivating flask 300, 400, 500 and 600 and how they connect to one another have been described above with respect to FIGS.

3A–6B. However, for clarity, the cell cultivating flask 300 is the only cell cultivating flask described below with respect to the preferred method 700.

Beginning at step 702, the cell cultivating flask 300 is partially filled with a cell cultivating media including both nutrients and cells. In fact, the cell cultivating flask 300 can be filled with any liquid cell culture media including, for example, Delbecco's MEM, Ham's F12 and Eagles' MEM. Moreover, the cell cultivating flask 300, 400, 500 and 600 can be used with any of the anchorage dependent cell lines including, for example, HEK293, CHO and HeLa.

In particular, the cell cultivating flask 300 can be partially filled with the cell cultivating media in one of two ways which are described below with respect to steps 702a and 702b. At step 702a, the user can use the pipette 345 (e.g., a 25 ml or smaller pipette) to directly add the cell cultivating media to one of the trays 320, 330 and 340 (e.g., intermediate tray 320). The user can then use the pipette 345 to add the cell cultivating media to another one of the trays 320, 330 and 340 (e.g., intermediate tray 330). Basically, the user can use the pipette 345 to directly add the cell cultivating media directly to each tray 320, 330 and 340 within the cell cultivating flask 300 (see FIG. 3H).

Figure 8A:
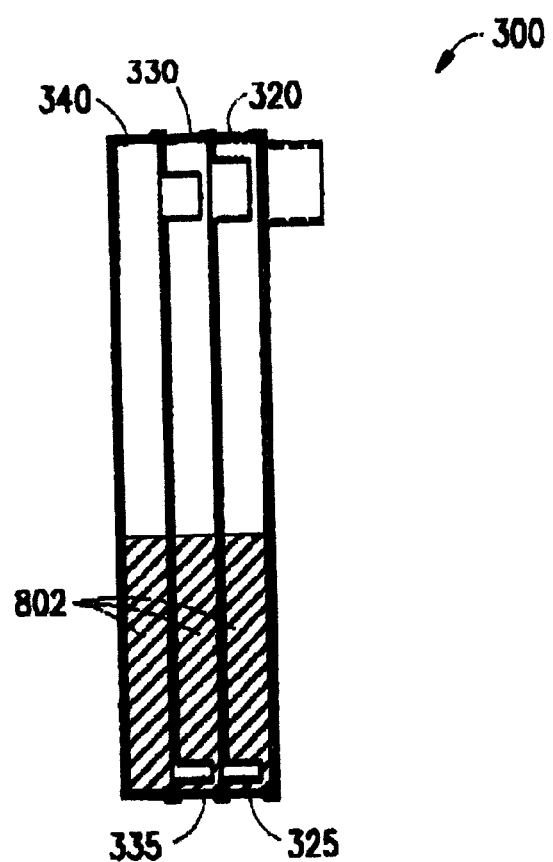
FIGS. 8A–8B illustrates cross sectional side views of the cell cultivating flask shown in FIG. 3A being filled in accordance with a filling operation of step 702b of the preferred method of FIG. 7.
Figure 8B:
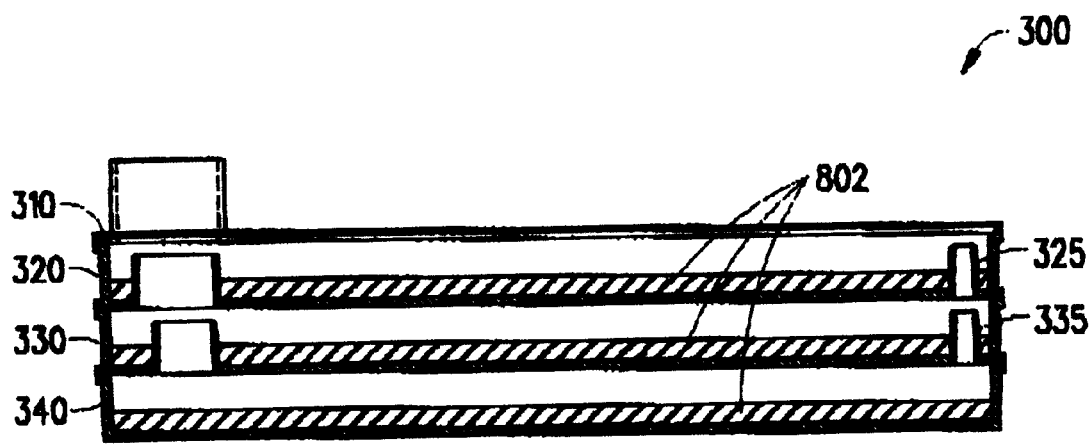

Alternatively, at step 702b, the user can use a filling bottle (or similar device) to add the cell cultivating media to each of the cell growth areas on the intermediate trays 320 and 330 and the bottom tray 340 at the same time. Referring to FIGS. 8A–8B, there are illustrated two cross sectional side views of the cell cultivating flask 300 being filled with cell cultivating media 802 in accordance with the filling step 702b. Basically, the filing bottle (not shown) containing the cell cultivating media 802 is used to pour the cell cultivating media 802 into the cell cultivating flask 300. The cell cultivating flask 300 is then orientated into a vertical position which enables the cell cultivating media to evenly distribute itself within each of the trays 320, 330 and 340 with the aid of the exchange tubes 325 and 335 (see FIG. 8A). Thereafter, the cell cultivating flask 300 is orientated into a horizontal position which enables the cell cultivating media to evenly distribute itself within each of the trays 320, 330 and 340 with the aid of the exchange tubes 325 and 335 (see FIG. 8B). It should be noted that the user could use the additional neck 602 in the cell cultivating flask 600 to initially pour the cell cultivating media 802 into a vertical cell cultivating flask 600 (see FIG. 6A).

At step 704, the user maintains the atmospheric properties (e.g., temperature) needed to enable the cells within the cell cultivating media to grow. To accomplish this, the cell cultivating flask 300 could be placed into an incubator (not shown). It should be understood that the user can also use the pipette 345 to add additional cell cultivating media to the individual trays 320, 330 and 340 within the cell cultivating flask 300 at this time.

At step 706, the user recovers at least a portion of the cultivating cell media including the grown cells from the cell cultivating flask 300. In particular, the cell cultivating media can be removed from the cell cultivating flask 300 in one of two ways which are described below with respect to steps 706a and 706b. At step 706a, the user can use the pipette 345 (e.g., a 25 ml or smaller pipette) to directly remove some or all of the cell cultivating media from one of the trays 320, 330 and 340 (e.g., intermediate tray 320). The user can then use the pipette 345 to directly remove some or all of the cell cultivating media from another one of the trays 320, 330 and 340 (e.g., intermediate tray 330). Basically, the user can use the pipette 345 to remove some or all of the cell cultivating media directly from each of the tray 320, 330 and 340 within the cell cultivating flask 300 (see FIG. 3H).

Alternatively, at step 706b, the user can recover all of the cultivating cell media including the grown cells from the cell cultivating flask 300. Referring to FIGS. 9A–9C, there are illustrated three cross sectional side views of the cell cultivating flask 300 being emptied of cell cultivating media 802 in accordance with the recovering step 706b. Basically, the user tilts the cell cultivating flask 300 upside down so as to drain most of the cell cultivating media 802 from the cell cultivating flask 300 (see FIG. 9A). The user then can tilt the cell cultivating flask 300 upside down so that the remaining cell cultivating media 802 collects into the corner of the intermediate tray 320 (see FIG. 9B). Thereafter, the user tilts the cell cultivating flask 300 in a manner so as to drain the remaining cell cultivating media 802 from the cell cultivating flask 300 (see FIG. 9C).

It should be understood that the cell cultivating flasks 300, 400, 500 and 600 could be any size such as, for example, 5.5 inches by 7 inches with a growing surface in each chamber or tray equal to the capacity of a Corning 225 cm2 flask to help with scaling up.

It should also be understood that one or more of the trays within the cell cultivating flasks 300, 400, 500 and 600 could have necks with openings that are the same size and located directly below one another. For instance, the cell cultivating flasks 300, 400, 500 and 600 could have a bottom tray and cover made in separate molds and two or more of the intermediate trays made in the same mold. In this case, the user would have direct access to the bottom tray and to the "top" intermediate tray of the intermediate trays that where made in the same mold.

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A cell cultivating flask comprising:
    a cover;
    at least one intermediate tray, each intermediate tray includes a bottom plate and side walls that define a cell growth area; and
    a bottom tray including a bottom plate and side walls that define a cell growth area, wherein said at least one intermediate tray is stacked on top of one another when there is more than one intermediate tray and said at least one intermediate tray is positioned between said cover and said bottom tray, and wherein said cover and said at least one intermediate tray each have a neck with an opening formed therein which enables a user to directly access each of the cell growth areas on said at least one intermediate tray and said bottom tray because said necks become progressively smaller in diameter as they move down from said cover through said at least one intermediate tray toward said bottom tray.

2. The cell cultivating flask of claim 1, wherein said user can use a pipette to add or remove a cell cultivating media to or from the cell growth areas on said at least one intermediate tray and said bottom tray.

3. The cell cultivating flask of claim 1, wherein said necks are offset from one another to allow greater access to the cell growth areas on said at least one intermediate tray and said bottom tray.

4. The cell cultivating flask of claim 1, wherein said necks are an integral part of the side walls in said at least one intermediate tray and said bottom tray.

5. The cell cultivating flask of claim 1, further comprising a vent cap which cooperates with the neck formed within said cover.

6. The cell cultivating flask of claim 5, wherein said vent cap is configured to allow gas to escape therefrom that was generated by growing cells.

7. The cell cultivating flask of claim 1, wherein each intermediate tray includes an exchange tube with an opening and each exchange tube extends up from a bottom plate of each intermediate tray.

8. The cell cultivating flask of claim 1, wherein said cover, said at least one intermediate tray and said bottom tray each have a notched corner which enables a plurality of cell cultivating flasks to be stacked on top of one another.

9. The cell cultivating flask of claim 1, further comprising an external neck in which said user can use to add or remove a cell cultivating media to or from said cell cultivating flask.

10. A method for growing cells, said method comprising the steps of:
adding a cell cultivating media to a first tray within a cell cultivating flask;
adding a cell cultivating media to a second tray within the cell cultivating flask, wherein said first and second trays each have a neck with an opening formed therein which enables a user to directly add the cell cultivating media to each of said first and second trays because said necks become progressively smaller in diameter as they move down from said first tray to said second tray;
maintaining properties suitable to grow cells within the first tray and the second tray of the cell cultivating flask;
recovering at least a portion of the cell cultivating media including the grown cells from the first tray of the cell cultivating flask; and
recovering at least a portion of the cell cultivating media including the grown cells from the second tray of the cell cultivating flask.

11. The method of claim 10, further comprising the step of directly adding a cell cultivating media to at least one more tray within the cell cultivating flask.

12. The method of claim 10, wherein said maintaining step further includes placing the cell cultivating flask into an incubator.

13. The method of claim 10, wherein a user can use a pipette to directly add the cell cultivating media to each tray in the cell cultivating flask.

14. A method for growing cells, said method comprising the steps of:
filling at least a portion of a flask with a cell cultivating media, wherein said flask includes:
a cover;
at least one intermediate tray, each of which includes a bottom plate and side walls that define a cell growth area; and
a bottom tray including a bottom plate and side walls that define a cell growth area, wherein each intermediate tray is positioned between said cover and said bottom tray, and wherein said cover and each intermediate tray have a neck with an opening formed therein which enables a user to directly access each of the cell growth areas on said at least one intermediate tray and said bottom tray because said necks become progressively smaller in diameter as they move down from said cover through said at least one intermediate tray toward said bottom tray;
maintaining properties suitable to grow cells within said flask; and
recovering at least a portion of the cell cultivating media including the grown cells from said flask.

15. The method of claim 14, wherein said filling step further includes directly adding the cell cultivating media to each of the cell growth areas within each tray of said flask.

16. The method of claim 15, wherein said directly adding step further includes enabling a user to use a pipette to directly add the cell cultivating media to each of the cell growth areas within each tray of said flask.

17. The method of claim 14, wherein said recovering step further includes enabling a user to use a pipette to directly remove at least a portion of the cell cultivating media including the grown cells from each of the cell growth areas within each tray of said flask.

18. The method of claim 14, wherein said filling step further includes adding the cell cultivating media to each of the cell growth areas on each tray of said flask at the same time.

19. The method of claim 18, wherein said adding step further includes pouring the cell cultivating media into said flask and orientating said flask into a vertical position and then orientating said flask into a horizontal position to evenly distribute the cell cultivating media among each tray of said flask.

20. The method of claim 14, wherein said recovering step further includes tilting said flask in a manner to drain at least a portion of the cell cultivating media including grown cells from said cell cultivating flask.

21. A flask used for growing cells, said flask comprising:
a cover;
an intermediate tray including a bottom plate and side walls that define a cell growth area; and
a bottom tray including a bottom plate and side walls that define a cell growth area, wherein said intermediate tray is positioned between said cover and said bottom tray and wherein said cover and said intermediate tray each have a neck with an opening formed therein which enables a user to directly add or remove a cell cultivating media to or from each of the cell growth areas in said intermediate tray and said bottom tray because said necks become progressively smaller in diameter as they move down from said cover through said intermediate tray toward said bottom tray.

22. The flask of claim 21, further comprising at least one more intermediate tray located between said cover and said bottom tray.

23. The flask of claim 21, wherein said user can use a pipette to add or remove the cell cultivating media to or from each of the cell growth areas in said intermediate tray and said bottom tray.

24. The flask of claim 21, wherein said cell cultivating media further includes nutrients and cells to be cultivated.

* * * * *